United States Patent
Lee et al.

(10) Patent No.: US 9,616,424 B2
(45) Date of Patent: Apr. 11, 2017

(54) CENTRIFUGAL-BASED MICROFLUIDIC APPARATUS, METHOD OF FABRICATING THE SAME, AND METHOD OF TESTING SAMPLES USING THE MICROFLUIDIC APPARATUS

(71) Applicant: SAMSUNG ELECTRONICS CO., LTD., Gyeonggi-do (KR)

(72) Inventors: Beom Seok Lee, Hwaseong-si (KR); Ji Won Kim, Suwon-si (KR); Jeong Gun Lee, Seoul (KR); Kui Hyun Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 216 days.

(21) Appl. No.: 13/730,554

(22) Filed: Dec. 28, 2012

(65) Prior Publication Data

US 2013/0115135 A1 May 9, 2013

Related U.S. Application Data

(62) Division of application No. 12/569,437, filed on Sep. 29, 2009, now Pat. No. 8,367,398.

(30) Foreign Application Priority Data

Oct. 1, 2008 (KR) .......................... 10-2008-0096724

(51) Int. Cl.
 *B01L 3/00* (2006.01)
 *G01N 21/07* (2006.01)
 (Continued)

(52) U.S. Cl.
 CPC ..... *B01L 3/50273* (2013.01); *B01L 3/502738* (2013.01); *G01N 21/07* (2013.01);
 (Continued)

(58) Field of Classification Search
 CPC .......... B01L 3/50273; B01L 3/502738; B01L 3/545; G01N 21/07; G01N 33/54386
 See application file for complete search history.

(56) References Cited

U.S. PATENT DOCUMENTS 3,787,290 A * 1/1974 Kaye .............................. 435/40
6,319,469 B1 11/2001 Mian et al.
(Continued)

FOREIGN PATENT DOCUMENTS

| CN | 1208464 A | 2/1999 |
|---|---|---|
| KR | 10-2008-0022035 A | 3/2008 |
| WO | 97/21090 A1 | 6/1997 |

OTHER PUBLICATIONS

Communication dated Jun. 4, 2012, issued by the European Patent Office, in counterpart European Application No. 09817962.5.
(Continued)

*Primary Examiner* — Melanie Y Brown
(74) *Attorney, Agent, or Firm* — Sughrue Mion, PLLC

(57) ABSTRACT

Provided is a microfluidic apparatus including: a microfluidic structure for providing spaces for receiving a fluid and for forming channels, through which the fluid flows; and valves for controlling the flow of fluid through the channels in the microfluidic apparatus. The microfluidic structure includes: a sample chamber; a sample separation unit receiving the sample from the sample chamber and separating a supernatant from the sample by using a centrifugal force; a testing unit receiving the supernatant from the sample separation unit for detecting a specimen from the supernatant using an antigen-antibody reaction, and a quality control chamber for identifying reliability of the test.

9 Claims, 15 Drawing Sheets

(51) Int. Cl.
  *G01N 33/543* (2006.01)
  *G01N 35/00* (2006.01)
(52) U.S. Cl.
  CPC . *G01N 33/54386* (2013.01); *G01N 35/00069* (2013.01); *B01L 3/545* (2013.01); *B01L 2200/0621* (2013.01); *B01L 2200/0689* (2013.01); *B01L 2200/10* (2013.01); *B01L 2300/021* (2013.01); *B01L 2300/0806* (2013.01); *B01L 2300/0816* (2013.01); *B01L 2300/0861* (2013.01); *B01L 2300/161* (2013.01); *B01L 2300/1827* (2013.01); *B01L 2400/0406* (2013.01); *B01L 2400/0409* (2013.01); *B01L 2400/0677* (2013.01)

(56) References Cited

U.S. PATENT DOCUMENTS

| | | |
|---|---|---|
| 2001/0048895 A1 | 12/2001 | Virtanen |
| 2001/0055812 A1 | 12/2001 | Mian et al. |
| 2002/0076354 A1* | 6/2002 | Cohen .............. 422/72 |
| 2003/0010792 A1 | 1/2003 | Forshey et al. |
| 2004/0089616 A1 | 5/2004 | Kellogg et al. |
| 2006/0009501 A1 | 1/2006 | Nair et al. |
| 2006/0073584 A1* | 4/2006 | Sasaki et al. .............. 435/288.5 |
| 2007/0161076 A1 | 7/2007 | Halden |
| 2008/0056949 A1 | 3/2008 | Lee et al. |
| 2008/0058991 A1 | 3/2008 | Lee et al. |
| 2008/0199930 A1* | 8/2008 | Lee ............... B01F 11/0266 435/173.1 |
| 2008/0300148 A1 | 12/2008 | Lee et al. |
| 2010/0240142 A1 | 9/2010 | Saiki et al. |

OTHER PUBLICATIONS

Communication from the Taiwanese Patent Office dated Mar. 4, 2013, in a counterpart application No. 098133137.

Communication dated Jul. 28, 2016 issued by Taiwanese Patent Office in counterpart Taiwan Patent Application No. 0901004334.

\* cited by examiner

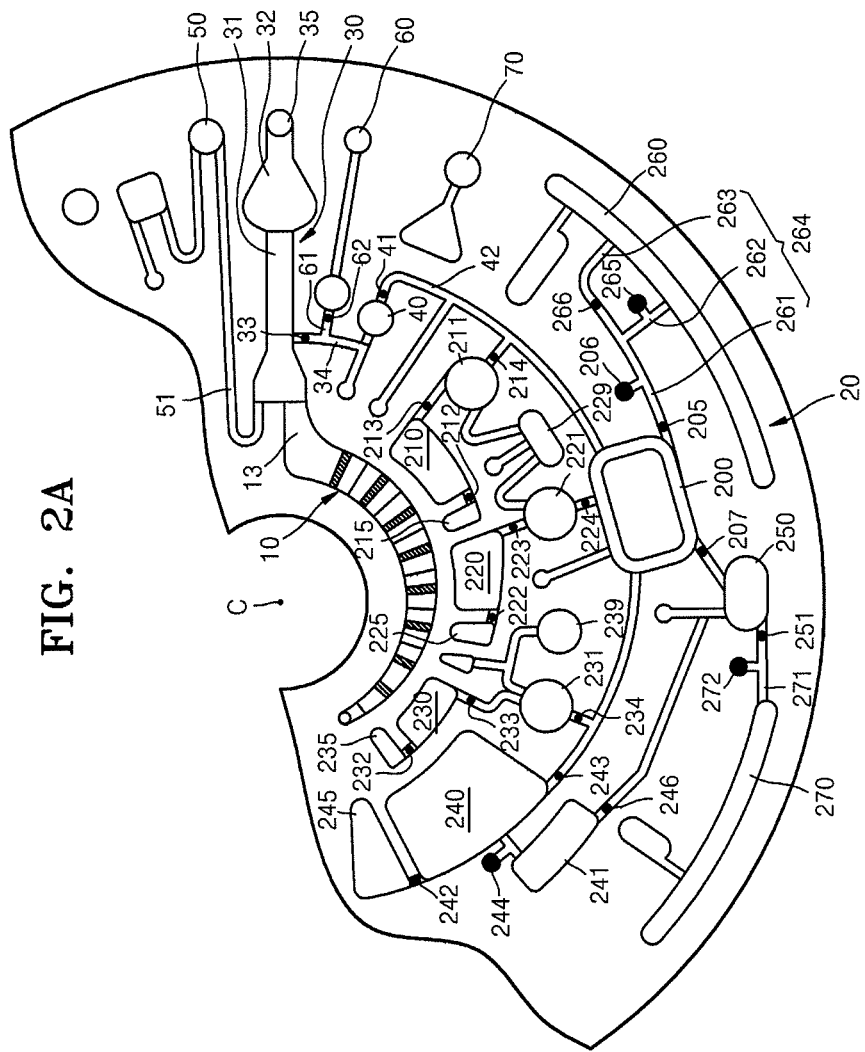

CENTRIFUGAL-BASED MICROFLUIDIC APPARATUS, METHOD OF FABRICATING THE SAME, AND METHOD OF TESTING SAMPLES USING THE MICROFLUIDIC APPARATUS

CROSS-REFERENCE TO RELATED APPLICATIONS

This is a Divisional of application Ser. No. 12/569,437 filed Sep. 29, 2009, which claims priority from Korean Patent Application No. 10-2008-0096724, filed on Oct. 1, 2008 in the Korean Intellectual Property Office, the disclosures of which are incorporated herein in their entirety by reference.

BACKGROUND

1. Field

One or more embodiments relate to a microfluidic apparatus based on a centrifugal force, a method of fabricating the microfluidic apparatus, and a method of testing samples using the microfluidic apparatus.

2. Description of the Related Art

Examples of microfluidic structures of a microfluidic device include a chamber which may accommodate a small amount of fluid, a channel through which the fluid may flow, a valve which may adjust the flow of the fluid, and various functional units which may accommodate the fluid and conduct predetermined functions. A small chip on which the microfluidic structures of a microfluidic device are mounted in order to perform various tests including a biochemical reaction is referred to as a biochip, and in particular, a device which is formed to perform various operations in one chip is referred to as a lab-on-a-chip.

Driving pressure is required to transport a fluid within the microfluidic structures of the microfluidic device, and a capillary pressure or a pressure provided by a pump is used as the driving pressure. Recently, microfluidic devices using centrifugal force by mounting microfluidic structures in a disk-shaped platform have been proposed. These devices are referred to as a lab-on-a-disk or a lab compact disk (CD).

SUMMARY

One or more embodiments include a microfluidic apparatus and a method of testing samples using an antigen-antibody reaction.

One or more embodiments include a microfluidic apparatus based on a centrifugal force, for improving reliability of sample testing processes, and a method of testing samples.

One or more embodiments include a method of fabricating a microfluidic apparatus, which may easily fabricate a valve for controlling the flow of a fluid in a microfluidic structure.

Additional aspects will be set forth in part in the description which follows and, in part, will be apparent from the description, or may be learned by practice of the presented embodiments.

According to an aspect of one or more embodiments, there is provided a microfluidic apparatus including: a microfluidic structure for providing spaces for receiving fluid and for forming channels, through which the fluid flows; and valves for controlling the flow of fluid through the channels in the microfluidic apparatus, wherein the microfluidic structure includes: a sample chamber; a sample separation unit receiving the sample from the sample chamber and separating a supernatant from the sample using a centrifugal force; a buffer chamber receiving reaction buffer; a washing buffer chamber receiving washing buffer; a reaction chamber connected to the sample separation unit, the buffer chamber, and the washing buffer chamber, and coated with capture antibodies for capturing a specimen; and a detection chamber connected to the reaction chamber for receiving a final reaction material, having a space in which absorbance is measured for testing the specimen.

The reaction chamber may include a reaction cartridge, on which the capture antibodies and antigens are coated.

The microfluidic apparatus may further include: a first waste chamber receiving impurities discarded from the reaction chamber; and a first waste channel connecting the reaction chamber to the first waste chamber, and having an end portion connected to the reaction chamber and two final ends that diverge from the end portion to be connected to the first waste chamber, wherein a closed valve and an open valve are disposed on the end portion, and an open valve and a closed valve are respectively disposed on the two final ends so that the reaction chamber and the first waste chamber are isolated from each other after discarding the impurities twice from the reaction chamber.

The microfluidic apparatus may further include: a blank chamber providing the detection chamber with a washing buffer for measuring a reference absorbance; a second waste chamber receiving the washing buffer discarded from the detection chamber; and a second waste channel connecting the detection chamber to the second waste chamber, wherein a closed valve and an open valve are disposed in the second waste channel so that the detection chamber and the second waste chamber are isolated from each other after discarding the washing buffer.

The buffer chamber may include: a first buffer chamber receiving one of a conjugate buffer for performing a sandwich immunoassay reaction and a competitive protein for performing a competitive immunoassay reaction; a second buffer chamber receiving a substrate buffer that represents a predetermined color due to a substrate reaction with a resultant of a conjugate reaction or the competitive immunoassay reaction; and a third buffer chamber receiving a stop buffer that stops the substrate reaction.

The microfluidic apparatus may further include: a vent chamber forming a vent path which allows the buffer chamber to access external air, wherein closed valves are formed between the buffer chamber and the vent chamber and at an outlet of the buffer chamber.

The microfluidic apparatus may further include: a buffer metering chamber for metering reaction buffer between the buffer chamber and the reaction chamber; and an excess buffer chamber receiving reaction buffer exceeding capacity of the buffer metering chamber.

The microfluidic apparatus may further include: a vent chamber forming a vent path which allows the washing buffer chamber to access external air, wherein closed valves are formed between the washing buffer chamber and the vent chamber and at an outlet of the washing buffer chamber.

The microfluidic apparatus may further include: a supernatant metering chamber located between the sample separation unit and the reaction chamber to meter an amount of the supernatant.

The microfluidic apparatus may further include: a first quality control (QC) chamber located at a final end of the sample separation unit for identifying whether the microfluidic apparatus is used or not by detecting absorbance.

The microfluidic apparatus may further include: a second QC chamber connected to the sample separation unit and receiving the sample exceeding a capacity of the sample separation unit.

The microfluidic apparatus may further include: a third QC chamber for detecting an absorbance of the supernatant, the third QC chamber connected to a channel that connects the reaction chamber to the sample separation unit to receive the supernatant from the sample separation unit.

The microfluidic apparatus may further include: a fourth QC chamber receiving a material, absorbance of which varies depending on temperature.

The microfluidic apparatus may further include: a rotatable platform on which the microfluidic structure is formed. The platform may include a partition plate, on which an engraved structure providing spaces for receiving the fluid and for forming channels through which the fluid flows and having an opened upper portion is formed, and an upper plate coupled to the upper portion of the partition plate to block the upper portion of the engraved structure.

The valves may include a valve material that is melted by electromagnetic wave energy. The valve material may be a phase transition material, a phase of which is changed by the electromagnetic wave energy, or a thermosetting resin. The valve material may include fine heating particles dispersed in the phase transition material to generate heat by absorbing the electromagnetic wave energy.

According to another aspect of one or more embodiments, there is provided a microfluidic apparatus including: a microfluidic structure for providing spaces for receiving fluid and for forming channels through which the fluid flows; and valves for controlling the flow of fluid through the channels in the microfluidic structure, wherein the microfluidic structure includes: a sample chamber; a sample separation unit receiving the sample from the sample chamber and separating a supernatant from the sample by using a centrifugal force; a testing unit including a detection chamber, in which a resultant of an antigen-antibody reaction between the supernatant, capture antibody or capture antigen, and a reaction buffer is received; and a QC chamber for identifying reliability in specimen detection.

The QC chamber may include a first QC chamber located at a final end of the sample separation unit for identifying whether the microfluidic apparatus is used or not by detecting absorbance.

The microfluidic apparatus may further include: a second QC chamber connected to the sample separation unit, receiving the sample exceeding a capacity of the sample separation unit.

The microfluidic apparatus may further include: a third QC chamber connected to a channel that connects the reaction chamber to the sample separation unit to detect a state of the supernatant.

The microfluidic apparatus may further include: a fourth QC chamber receiving a material, absorbance of which varies depending on temperature.

The microfluidic apparatus may further include: a rotatable platform on which the microfluidic structure is formed. The detection chamber and the QC chamber may be located at the same distances from a center of rotation in a radial direction of the platform. The platform may include a partition plate, on which an engraved structure providing spaces for receiving the fluid and for forming channels through which the fluid flows and having an opened upper portion is formed, and an upper plate coupled to the upper portion of the partition plate to block the upper portion of the engraved structure. The upper plate may include a protective unit for protecting regions corresponding to the detection chamber and the QC chamber from being contaminated. The protective unit may include ribs surrounding the regions corresponding to the detection chamber and the QC chamber.

According to another aspect of one or more embodiments, there is provided a microfluidic apparatus including: a microfluidic structure for providing spaces for receiving fluid and for forming channels through which the fluid flows; and valves for controlling the flow of fluid through the channels in the microfluidic structure, wherein the microfluidic structure includes: a sample chamber; a sample separation unit receiving the sample from the sample chamber and separating a supernatant from the sample by using a centrifugal force; a testing unit including a detection chamber, in which a resultant of an antigen-antibody reaction between the supernatant, the capture antibody, and reaction buffer is received; and a temperature detection chamber including a material, absorbance of which varies depending on temperature.

According to another aspect of one or more embodiments, there is provided a method of fabricating a microfluidic apparatus, the method including: preparing a partition plate including an engraved structure which provides spaces for receiving fluid and channels through which the fluid flows and includes an open upper portion; preparing an upper plate; applying a valve material onto a plurality of locations, where valves control the flow of fluid through the channels, of a lower surface of the upper plate; coupling the upper plate to the partition plate to block the open upper portion, and forming a plurality of open valves; and forming a closed valve by applying energy to at least one of the plurality of open valves to melt the valve material and block the channel.

The valve material may be melted by electromagnetic wave energy. The valve material may be a phase transition material, a phase of which is changed by the electromagnetic wave energy, or a thermosetting resin. The valve material may include fine heating particles dispersed in the phase transition material to generate heat by absorbing the electromagnetic wave energy.

According to another aspect of one or more embodiments, there is provided a method of testing a specimen, which tests specimens included in a sample by separating a supernatant from the sample, performing an antigen-antibody reaction between the supernatant and a reaction buffer, and receiving a resultant of the reaction in a detection chamber and measuring absorbance of the resultant using a microfluidic apparatus including a sample chamber, a sample separation unit, and a testing unit, and receiving the reaction buffer and a washing buffer, the method including: loading the sample into the sample chamber of the microfluidic apparatus; mounting the microfluidic apparatus onto a rotation driver; and determining whether the microfluidic apparatus is already used or not by measuring an absorbance of a first QC chamber that is located at an end portion of the sample separation unit by using a detector.

The method may further include: conveying the sample from the sample chamber to the sample separation unit by a centrifugal force that is generated by the microfluidic apparatus rotated using the rotation driver; and determining whether an amount of the sample is sufficient or not by measuring absorbance of a second QC chamber which receives the sample exceeding the capacity of the sample separation unit using the detector.

The method may further include: determining whether a temperature of the microfluidic apparatus is appropriate for starting the test by measuring absorbance of a fourth QC chamber, the absorbance of which varies depending on the temperature, by using the detector.

The method may further include: centrifugating the supernatant from the sample received in the sample separation unit by rotating the microfluidic apparatus by using the rotation driver; conveying the supernatant to the testing unit; measuring absorbance of a third QC chamber that diverges from a channel connecting the sample separation unit to the testing unit by using the detector; and determining whether the amount of supernatant is sufficient, whether a state of the supernatant is suitable for the test, or whether a valve located between the sample separation unit and the testing unit is defective, based on the measured absorbance.

The method may further include: performing the antigen-antibody reaction between the supernatant, capture antibody, and the reaction buffer in a reaction chamber to form the reaction resultant; determining a reference absorbance by measuring the absorbance of the detection chamber; conveying the reaction resultant to the detection chamber and measuring the absorbance of the detection chamber; and calculating a concentration of the specimen from a difference between the reference absorbance and the measured absorbance. The measuring of the reference absorbance may include supplying the washing buffer to the detection chamber and measuring the absorbance of the detection chamber.

The method may further include: obtaining information regarding at least one of a fabrication date of the microfluidic apparatus, a term of validity of the microfluidic apparatus, and a relation between the measured absorbance and the concentration of the specimen from a barcode formed on a side portion of the microfluidic apparatus, by using a barcode reader.

BRIEF DESCRIPTION OF THE DRAWINGS

The above and/or other aspects will become apparent and more readily appreciated from the following description of the embodiments, taken in conjunction with the accompanying drawings of which:

FIG. 2A is a detail view of a testing unit included in the microfluidic apparatus of FIG. 1;

DETAILED DESCRIPTION

Figure 1:
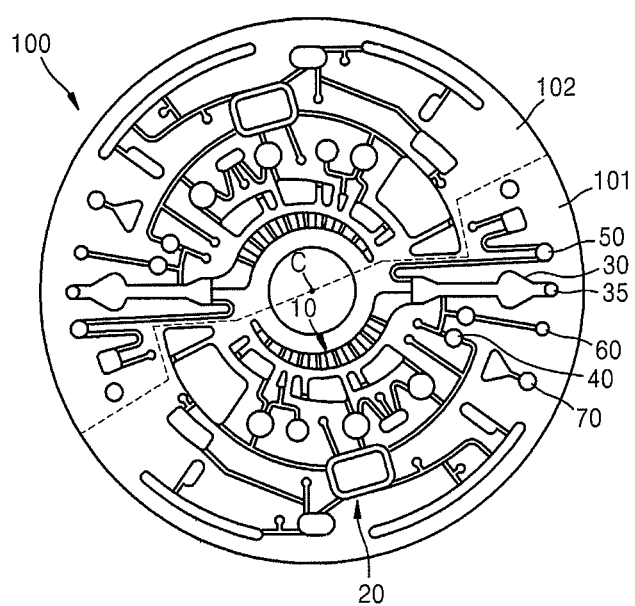
FIG. 1 is a plan view of a microfluidic apparatus according to an embodiment.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

FIG. 1 is a plan view of a microfluidic apparatus according to an embodiment; and FIG. 2A is a detail view of a microfluidic structure shown in FIG. 1. The microfluidic apparatus based on a centrifugal force according to the present embodiment may include a platform 100 that is a rotatable disk. The platform 100 includes a space for receiving a fluid, and a microfluidic structure for providing a fluid path. The platform 100 is not limited to the disk shape. The platform 100 may be formed of a plastic material such as acryl or polydimethylsiloxane (PDMS) which may be molded easily and has a biologically inert surface. However, the present embodiment is not limited to the above example, and the platform 100 may be formed of a material having chemical and biological stability, optical transparency, and mechanical processability. The platform 100 may include a plurality of plates. An engraved structure corresponding to a chamber or a channel is formed in a surface of a plate, which faces another plate, and then, the plates are bonded to each other to provide a space for receiving the fluid and the fluid path in the platform 100. The bonding of the plates may be performed using an adhesive or a dual-adhesive tape, ultrasonic wave, or laser.

The platform 100 may include one or more microfluidic structures. For example, the platform 100 may be divided into a plurality of regions, and a microfluidic structure which operates independently may be installed in each of the regions. According to the microfluidic apparatus of the present embodiment, the microfluidic structures are respectively installed on two regions 101 and 102 of the platform 100 to detect specimens from a sample, for example, blood, through an antigen-antibody reaction. Since the microfluidic structures installed in the two regions 101 and 102 are substantially the same as each other except for the specimens to be detected, the microfluidic structure installed in the region 101 will be described in more detail.

Referring to FIG. 2A, a sample chamber 10, a sample separation unit 30, and a testing unit 20 are formed. The sample chamber 10 provides a space for receiving a liquid sample, for example, blood. The sample separation unit 30 performs centrifugation to divide the sample into a supernatant (for example, blood serum or blood plasma) and a precipitate (for example, blood cells). The testing unit 20 is a structure for detecting certain protein included in the supernatant using the antigen-antibody reaction, for example, detecting prostate specific antigen (PSA) and testosterone for detecting prostate cancer, or detecting thyroid stimulating hormone (TSH) or free T4 (fT4) protein for testing thyroid disease. The testing unit 20 of the present embodiment may detect the protein using a sandwich immunoassay method or a competitive immunoassy method.

Figure 2B:
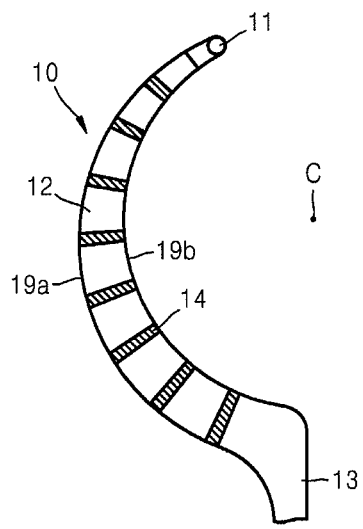
FIG. 2B is a detail view of a sample chamber included in the microfluidic apparatus of FIG. 1.

FIG. 2B shows the sample chamber 10 in detail. Referring to FIG. 2B, the sample chamber 10 includes an inlet 11 for injecting samples, and a receiving portion 12 for receiving the sample. The receiving portion 12 includes an outlet 13 connected to the sample separation unit 30. The outlet 13 may form a capillary pressure so that the sample may not move to the sample separation unit 30 when the centrifugal force is not applied, as will be described later. The outlet 13 may include a valve for controlling the flow of the sample. In addition, in order to easily induce the samples received in the receiving portion 12 by the centrifugal force into the sample separation unit 30, a side wall 19a that is located farther from a center C between two side walls 19a and 19b in a radial direction of the receiving portion 12 is formed so that a distance from the center C may increase from the inlet 11 to the outlet 13. A structure, which makes the sample flow to the receiving portion 12 due to an injection pressure of the sample and prevents the sample reaching the receiving portion 12 from returning to the inlet 11, that is, a structure performing as a capillary valve that passes the sample only when a pressure of a predetermined level is applied, may be formed between the inlet 11 and the receiving portion 12.

A backflow prevention unit 14 may be disposed in the receiving portion 12 in a direction crossing a flowing direction of the sample which flows from the inlet 12 to the outlet 13. The backflow prevention unit 14 may be formed as one or more ribs. The backflow prevention unit 14 acts as a flow resistance to the sample so that the sample is prevented from flowing from the receiving portion 12 to the inlet 11.

Figure 2C:
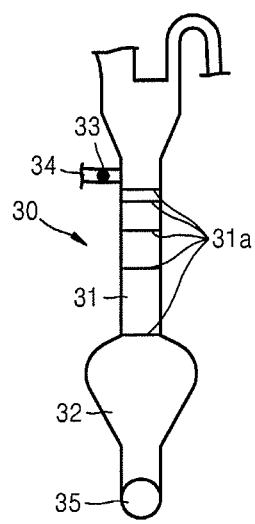
FIG. 2C is a detail view of a sample separation unit included in the microfluidic apparatus of FIG. 1.

The sample is conveyed from the sample chamber 10 to the sample separation unit 30 by the centrifugal force generated by the rotation of the platform 100, and thus, the sample separation unit 30 is located on an outer portion of the sample chamber 10. The sample separation unit 30 for centrifugating the sample may be formed in various shapes, and an example of the sample separation unit 30 is shown in FIG. 2C in detail. Referring to FIG. 2C, the sample separation unit 30 includes a supernatant collecting unit 31 formed as a channel extending radially from the sample chamber 10 toward the outside, and a precipitate collecting unit 32 located at an end portion of the supernatant collecting unit 31 to provide a space for collecting precipitates of a large specific gravity. The supernatant collecting unit 31 includes a sample distributing channel 34 for distributing the supernatant to the testing unit 20. A valve 33 controls the flow of the sample through the sample distributing channel 34. Various types of microfluidic valves may be adopted as the valve 33. The valve 33 of the present embodiment is a normally closed valve that closes the channel 34 so as to not allow the fluid to flow, before being opened due to an external power source. Referring to FIG. 2C, a plurality of stepped portions 31a may be formed in the supernatant collecting unit 31. The plurality of stepped portions 31a may denote a separation level of, for example, serum. The plurality of stepped portions 31a may represent separation levels of 40%, 35%, 32%, 30%, and 28% from the bottom. The separation level may be an element for checking the state of blood taken from a patient or a health condition of the patient.

Next, the testing unit 20 will be described in detail. Referring to FIG. 2A, a supernatant metering chamber 40, a reaction chamber 200, first, second, and third buffer chambers 210, 220, and 230, a washing buffer chamber 240, and a detection chamber 250 are shown.

The supernatant metering chamber 40 for metering an amount of the supernatant may be disposed between the sample separation unit 30 and the testing unit 20. The supernatant metering chamber 40 has an internal space that may receive the amount of supernatant used in the testing. The supernatant metering chamber 40 includes a valve 41 for controlling the flow of fluid on an outlet thereof. The valve 41 is a normally closed valve, like the valve 33. The supernatant metering chamber 40 is connected to the testing unit 20 through a channel 42.

The first, second, and third buffer chambers 210, 220, and 230 receive a reaction buffer used in the antigen-antibody reaction.

Figure 2D:
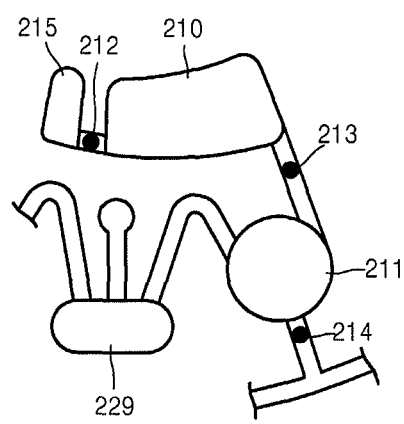
FIG. 2D is a detail view of a first buffer chamber included in the microfluidic apparatus of FIG. 1.

FIG. 2D shows a peripheral structure of the buffer chamber 210 in detail. Referring to FIG. 2D, the first buffer chamber 210 receives a first buffer. The first buffer may be a conjugate buffer for performing sandwich immunoassay or may include a competitive protein for performing competitive immunoassy. The first buffer chamber 210 is connected to a first vent chamber 215. The first vent chamber 215 forms a vent path which allows the first buffer chamber 210 to access external air so that the first buffer received in the first buffer chamber 210 may be discharged easily. A valve 212 is disposed between the first buffer chamber 210 and the first vent chamber 215. A valve 213 is disposed at an outlet of the first buffer chamber 210. The valves 212 and 213 are normally closed valves. The first buffer is loaded into the first buffer chamber 210 and the valves 212 and 213 are installed, and then, the first buffer chamber 210 is maintained in the closed state before opening the valves 212 and 213. A first metering chamber 211 is for supplying a fixed amount of first buffer that is used in the testing, to the reaction chamber 200. The first metering chamber 211 is connected to the first buffer chamber 210 through the valve 213. A valve 214 is disposed in an outlet of the first metering chamber 211. The valve 214 is normally closed. When the valve 214 opens, the first buffer that is metered by the first metering chamber 211 may be supplied to the reaction chamber 200.

A peripheral structure around the second buffer chamber 220, the third buffer chamber 230, and the washing buffer chamber 240 is similar to that of the first buffer chamber 210. Referring to FIG. 2A, the second buffer chamber 220 receives a second buffer. The second buffer may be a substrate buffer that represents a predetermined color due to a substrate reaction with a resultant of the conjugate reaction or the competitive reaction. The second buffer chamber 220 is connected to a second vent chamber 225. The second vent chamber 225 forms a vent path that allows the second buffer chamber 220 to access the external air so that the second buffer received in the second buffer chamber 210 may be discharged easily. A valve 222 is disposed between the second buffer chamber 220 and the second vent chamber 225. A valve 223 is disposed in an outlet of the second buffer chamber 220. The valves 222 and 223 are normally closed. The second buffer is loaded into the second buffer chamber 220 and the valves 222 and 223 are installed, and then, the second buffer chamber 220 maintains the closed state before opening the valves 222 and 223. A second metering chamber 221 is for supplying a fixed amount of the second buffer that is used in the testing to the reaction chamber 200. The second metering chamber 221 is connected to the second buffer chamber 220 through the valve 223. A valve 224 is disposed at an outlet of the second metering chamber 221. The valve 224 is the normally closed valve. When the valve 224 opens, the second buffer metered by the second metering chamber 221 may be supplied to the reaction chamber 200.

A first excessive buffer chamber 229 is connected to the first and second metering chambers 211 and 221. Portions of the first and second buffers exceeding the capacities of the first and second metering chambers 211 and 221 are received in the first excess buffer chamber 229.

The third buffer chamber 230 receives a third buffer. The third buffer may be a buffer for stopping the substrate reaction, that is, a stop solution. The third buffer chamber 230 is connected to a third vent chamber 235. The third vent chamber 235 forms a vent path that allows the third buffer chamber 230 to access the external air so that the third buffer received in the third buffer chamber 230 may be discharged easily. A valve 232 is disposed between the third buffer chamber 230 and the third vent chamber 235. A valve 233 is disposed at an outlet of the third buffer chamber 230. The valves 232 and 233 are normally closed. The third buffer is loaded into the third buffer chamber 230 and the valves 232 and 233 are installed, and then, the third buffer chamber 230 is maintained in the closed state before opening the valves 232 and 233. A third metering chamber 231 is for supplying the fixed amount of third buffer that is used in the testing to the reaction chamber 200. The third metering chamber 231 is connected to the third buffer chamber 230 through the valve 233. A valve 234 is disposed in an outlet of the third metering chamber 231. The valve 234 is normally closed. When the valve 234 opens, the fixed amount of third buffer that is metered by the third metering chamber 231 may be supplied to the reaction chamber 200.

A second excess buffer chamber 239 is connected to the third metering chamber 231. The third buffer exceeding the capacity of the third metering chamber 231 is received in the second excess buffer chamber 239.

The washing buffer chamber 240 may receive a washing buffer which washes away residuals after performing the antigen-antibody reaction. The washing buffer chamber 240 is connected to a fourth vent chamber 245. The fourth vent chamber 245 forms a vent path that allows the washing buffer chamber 240 to access the external air so that the washing buffer received in the washing buffer chamber 240 may be discharge easily. A valve 242 is disposed between the washing buffer chamber 240 and the fourth vent chamber 245. The washing buffer chamber 240 is connected to the reaction chamber 200 through a valve 243. The valves 242 and 243 are normally closed. In addition, the washing buffer chamber 240 may be connected to a blank chamber 241 through a valve 244. The blank chamber 241 may be connected to the detection chamber 250 through a valve 246. The valve 244 is normally open. The open valve closes a channel by receiving a driving power from the outside, and opens the channel before receiving the driving power so that the fluid may flow. Therefore, the washing buffer is received in the washing buffer chamber 240 and the blank chamber 241. The valve 246 is normally closed. The washing buffer is loaded into the washing buffer chamber 240 and the valves 242, 243, and 246 are installed, and then, the washing buffer chamber 240 is maintained in the closed state before opening the valves 242, 243, and 246.

Figure 3A:
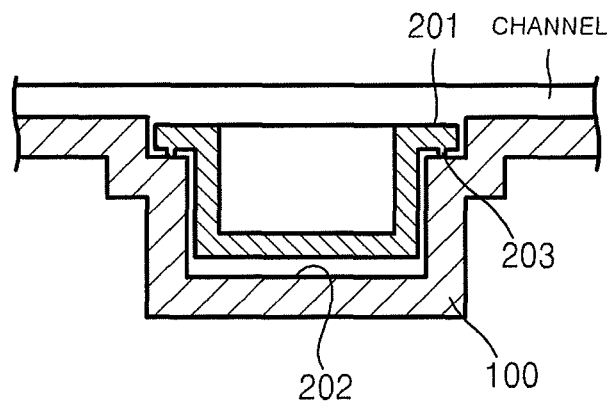
FIGS. 3A and 3B are cross-sectional views showing a reaction cartridge coupling to a platform in the microfluidic apparatus of FIG. 1.

The reaction chamber 200 receives the supernatant from the supernatant metering chamber 40 through a channel 42. The reaction chamber 200 includes capture antibodies or capture antigens for performing the antigen-antibody reaction with the sample. For example, the reaction chamber 200 may be formed by coupling a reaction cartridge 201 coated with capture antibodies to a mounting portion 202 installed in the platform 100 as shown in FIG. 3A. The reaction cartridge 201 may be coupled to the platform 100 by using various methods such as ultrasonic wave fusion, hot-melt bonding, or laser bonding. Reference numeral 203 denotes a fusion protrusion. For example, when the ultrasonic wave fusion is performed, the fusion protrusion 203 is melted by the ultrasonic wave energy and hardened so that the reaction cartridge 201 is coupled to the platform 100. The fusion protrusion 203 may be disposed on side portions of the reaction cartridge 201.

A first waste chamber 260 receives impurities discarded from the reaction chamber 200. An end 261 of a first waste channel 264 is connected to the reaction chamber 200, and two final portions 262 and 263 of the first waste channel 264 diverge from the end 261 and are connected to the first waste chamber 260. Valves 205 and 206 are disposed at the end portion 261 of the first waste channel 264, and a valve 265 and a valve 266 are respectively disposed at the two final portions 262 and 263. The valves 205 and 266 are the normally closed valves, and the valves 206 and 265 are the normally open valves.

The detection chamber 250 is connected to the reaction chamber 200 through a valve 207, and receives the final fluid, the reaction of which is finished, from the reaction chamber 200. In addition, as described above, the detection chamber 250 is connected to the blank chamber 241 to be provided with the washing buffer.

A second waste chamber 270 is connected to the detection chamber 250 through a second waste channel 271. Valves 251 and 272 are formed in the second waste channel 271. The valve 251 is the normally closed valve, and the valve 272 is the normally open valve.

Referring to FIG. 2A, quality control (QC) chambers, which ensure reliability of the sample analysis, will now be described.

A first QC chamber 35 is disposed at an end portion of the sample separation unit 30 for detecting whether the microfluidic apparatus has been previously used. Before supplying the sample from the sample chamber 10 to the sample separation unit 30, an absorbance of the first QC chamber 35 is measured using a detector (520 of FIG. 10) that will be described later so as to check whether the sample is in the first QC chamber 35, and thus, it may be detected whether the microfluidic apparatus has been previously used.

A second QC chamber 50 is provided to identify whether a sufficient amount of sample used to perform the testing is supplied to the sample separation unit 30. The second QC chamber 50 is connected to an upper end of the sample separation unit 30 through a channel 51. A portion of the sample exceeding the capacity of the sample separation unit 30 is moved to the second QC chamber 50 through the channel 51. After supplying the sample from the sample chamber 10 to the sample separation unit 30 and before performing the centrifugating operation, absorbance of the second QC chamber 50 is measured using the detector (520 of FIG. 10) to check whether the sample is in the second QC chamber 50, and thus, it may be checked whether the sample is supplied in the amount required to the sample separation unit 30.

A third QC chamber 60 is provided to identify whether the centrifugation by the sample separation unit 30 is appropriately performed. The third QC chamber 60 is connected to the supernatant collecting unit 31 of the sample separation unit 30 through the sample distributing channel 34 and a channel 61. When the valve 33 is opened, the supernatant fills the third QC chamber 60. Absorbance of the third QC chamber 60 is measured using the detector (520 of FIG. 10).

When the measured absorbance represents a reference absorbance that denotes that the supernatant sufficiently fills the third QC chamber 60, it implies that the centrifugation performed by the sample separation unit 30 is normally performed. When the measured absorbance is greater than the reference absorbance, the centrifugation of the sample is not performed normally and impurities are included in the supernatant or the sample is defective. In addition, when the third QC chamber 60 is not completely filled with the supernatant, the supernatant may include air pores, and in this case, the absorbance is greater than the reference absorbance. Therefore, the lack of the supernatant may be identified. In addition, the operation of the valve 33 may be identified by measuring the absorbance of the third QC chamber 60. That is, when the measured absorbance denotes the empty state of the third QC chamber 60, it implies that the valve 33 does not operate properly. A valve 62 may be disposed in the channel 61. The valve 62 is the normally closed valve. The valve 62 may be opened after the supernatant is moved to the supernatant metering chamber 40 when the valve 33 is opened.

A fourth QC chamber 70 is a temperature detection chamber for detecting whether a temperature of the sample is appropriate for the testing. To do this, a material whose absorbance varies according to the temperature may be loaded into the fourth QC chamber 70. For example, thyon dye may be loaded into the fourth QC chamber 70. The absorbance of the fourth QC chamber 70 is measured using the detector (520 of FIG. 10) to identify whether the temperature of the microfluidic apparatus is appropriate for performing the testing.

The washing buffer is loaded into the detection chamber 250 through the blank chamber 241 in order to check the state of the detection chamber 250. Contamination of the detection chamber 250 affects the detection of the final absorbance. A chamber (not shown) may be formed besides the detection chamber 250 and absorbance of this chamber may be used as the reference absorbance. However, in this case, the normal absorbance is not the absorbance of the detection chamber 250, in which the testing is actually performed, and thus, the reference absorbance does not denote the state of the detection chamber 250. In the present embodiment, a fixed amount of washing buffer is loaded into the detection chamber 250, and after that, the absorbance is measured using the detector (520 of FIG. 10). This measured absorbance becomes the reference absorbance that represents the state of the detection chamber 250. After discarding the washing buffer, the final fluid, the reaction of which is finished, is supplied from the reaction chamber 200 to the detection chamber 250 and the absorbance of the fluid is measured, and then, a difference between the measured absorbance and the reference absorbance may prevent the absorbance detection error that may be caused by the state of the detection chamber 250 which varies depending on the manufacturing status of the microfluidic apparatus.

Figure 10:
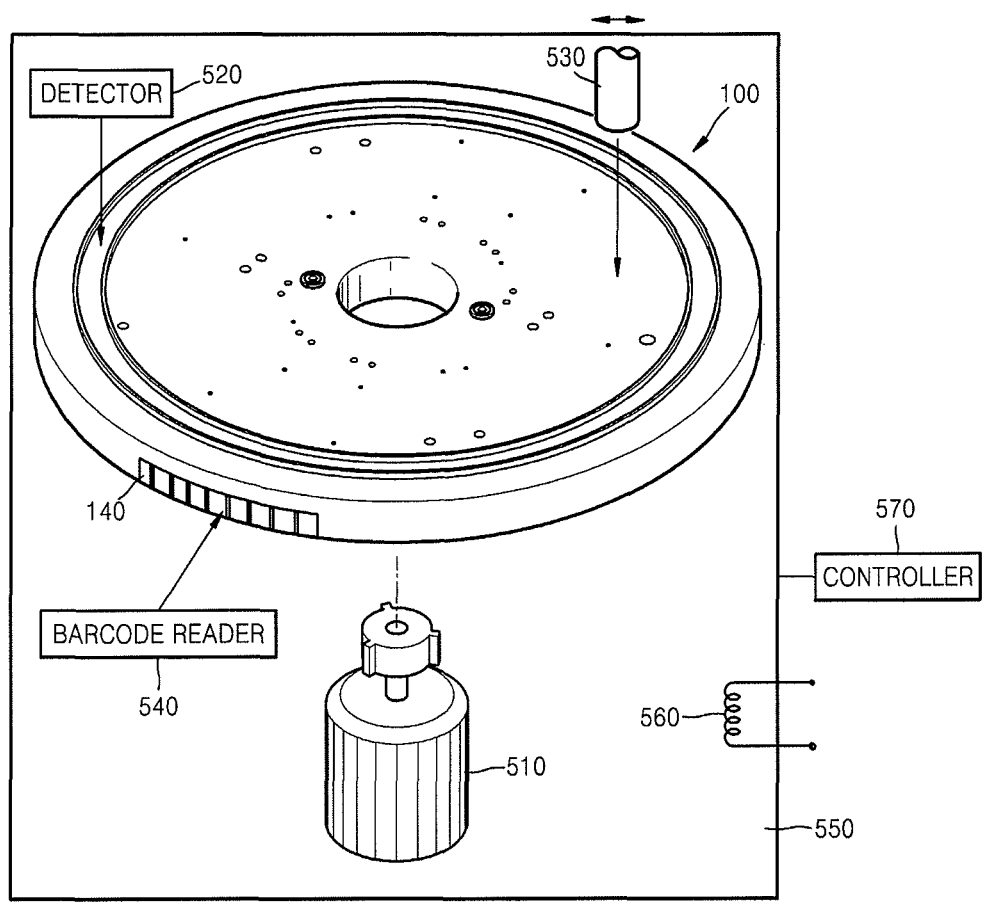
FIG. 10 is a diagram of an example of a sample analyzing system.

The first to fourth QC chambers 35, 50, 60, and 70 may be located at the same distance in a radial direction from the center C in order to minimize the movement of the detector (520 of FIG. 10).

The normally closed valve and the normally open valve will be described in detail. The normally open valve and the normally closed valve are valves which operate actively by receiving a driving power or energy from the outside. Hereinafter, operating principles of the normally closed valve and the normally open valve will be described, and processes of fabricating the valves will be described later.

Figure 4A:
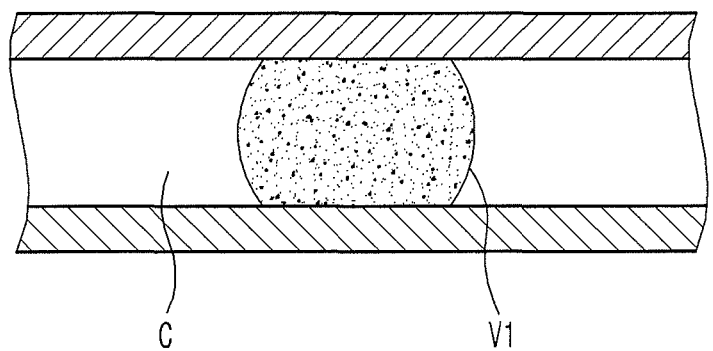
FIGS. 4A and 4B are cross-sectional views showing operations of a closed valve in the microfluidic apparatus of FIG. 1.
Figure 4B:
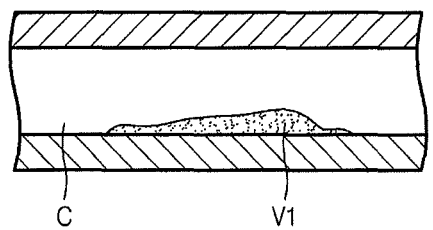

FIGS. 4A and 4B are cross-sectional views showing an example of the normally closed valve adopted in the microfluidic apparatus of FIG. 1. The normally closed valve may include a valve material V1 that is solid at room temperature. The valve material V1 exists in the channel C in a solid state to block the channel C as shown in FIG. 4A. The valve material V1 is melted at a high temperature and is moved in a space in the channel C, and then, coagulates while opening the channel C as shown in FIG. 4B. The energy irradiated from the outside may be electromagnetic waves, and an energy source may be a laser light source irradiating laser beams or a light emitting diode or a Xenon lamp irradiating visible rays or infrared rays. When the energy source is the laser light source, the energy source may include at least one laser diode. The external energy source may be selected according to a wavelength of the electromagnetic wave, which may be absorbed by a heating element included in the valve material V1. The valve material V1 may be a thermoplastic resin such as cyclic olefin copolymer (COC), polymethylmethacrylate (PMMA), polycarbonate (PC), polystyrene (PS), polyoxymethylene (POM), perfluoroalkoxy (PFA), polyvinylchloride (PVC), polypropylene (PP), polyethylene terephthalate (PET), polyetheretherketone (PEEK), polyamide (PA), polysulfone (PSU), and polyvinylidene fluoride (PVDF). In addition, a phase transition material that is in the solid state in the room temperature may be used as the valve material V1. The phase transition material may be wax. When the wax is heated, the wax is melted to a liquid state, and a volume of the wax increases. The wax may be paraffin wax, microcrystalline wax, synthetic wax, or natural wax. The phase transition material may be a gel or a thermoplastic resin. The gel may be polyacrylamide, polyacrylates, polymethacrylates, or polyvinylamides. In the valve material V1, a plurality of fine heating particles which absorb the electromagnetic wave energy to generate heat may be dispersed. Each of the fine heating particles may have a diameter of about 1 nm to about 100 µm so as to freely pass through the channel C having a depth of about 0.1 mm and a width of about 1 mm. When the electromagnetic energy is supplied to the fine heating particles through the laser beams, for example, the temperature of the fine heating particles rises rapidly to generate heat, and the fine heating particles are evenly dispersed in the wax. The fine heating particles may have a core including a metal component, and a hydrophobic surface structure. For example, the fine heating particle may have a molecular structure having a core formed of Fe and a plurality of surfactants surrounding Fe. The fine heating particles may be stored in carrier oil. The carrier oil may be also hydrophobic so that the fine heating particles having the hydrophobic surface structures may be evenly dispersed. The carrier oil, in which the fine heating particles are dispersed, is mixed with the melted phase transition material, and the mixed material is loaded into the channel C and coagulated to block the channel C. The fine heating particles are not limited to the polymer particles described above, and may be quantum dots or magnetic beads. In addition, the fine heating particles may be fine metal oxide materials, for example, $Al_2O_3$, $TiO_2$, $Ta_2O_3$, $Fe_2O_3$, $Fe_3O_4$, or $HfO_2$. On the other hand, the normally open valve does not necessarily include the fine heating particles, and may be formed of the phase transition material without including the fine heating particles.

Figure 5A:
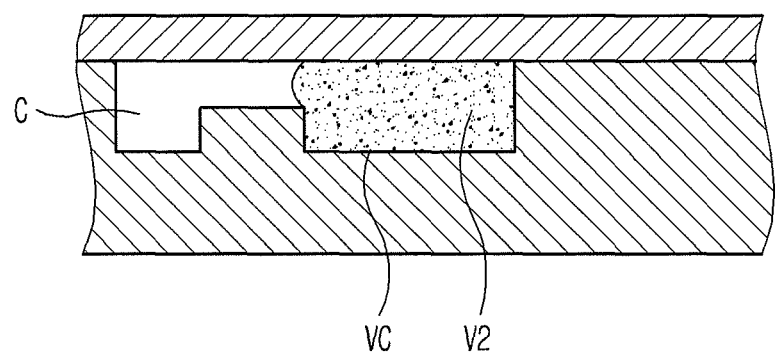
FIGS. 5A and 5B are cross-sectional views showing operations of an open valve in the microfluidic apparatus of FIG. 1.
Figure 5B:
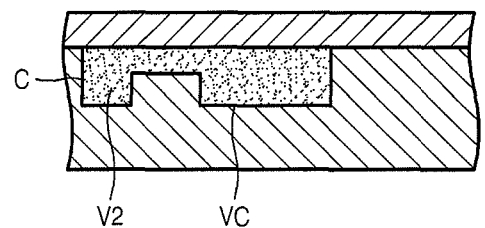

FIGS. 5A and 5B are cross-sectional views showing an example of the normally open valve. The normally open valve includes a channel C, a valve chamber VC connecting to a part of the channel C, and a valve material V2 filled in the valve chamber VC. The valve material V2 may be the same as the valve material V1 of the normally closed valve. Referring to FIG. 5A, before supplying the external energy to the valve, since the valve V2 exists in the valve chamber VC, and the channel C maintains an open state. Then, when the external energy is supplied to the valve material V2, the valve material is melted and expanded to be induced into the channel C, and the melted valve material V2 is coagulated to block the flow of the fluid through the channel C.

Figure 3B:
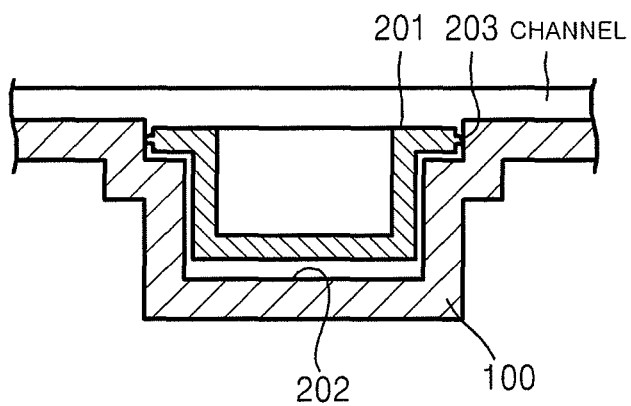
Figure 6:
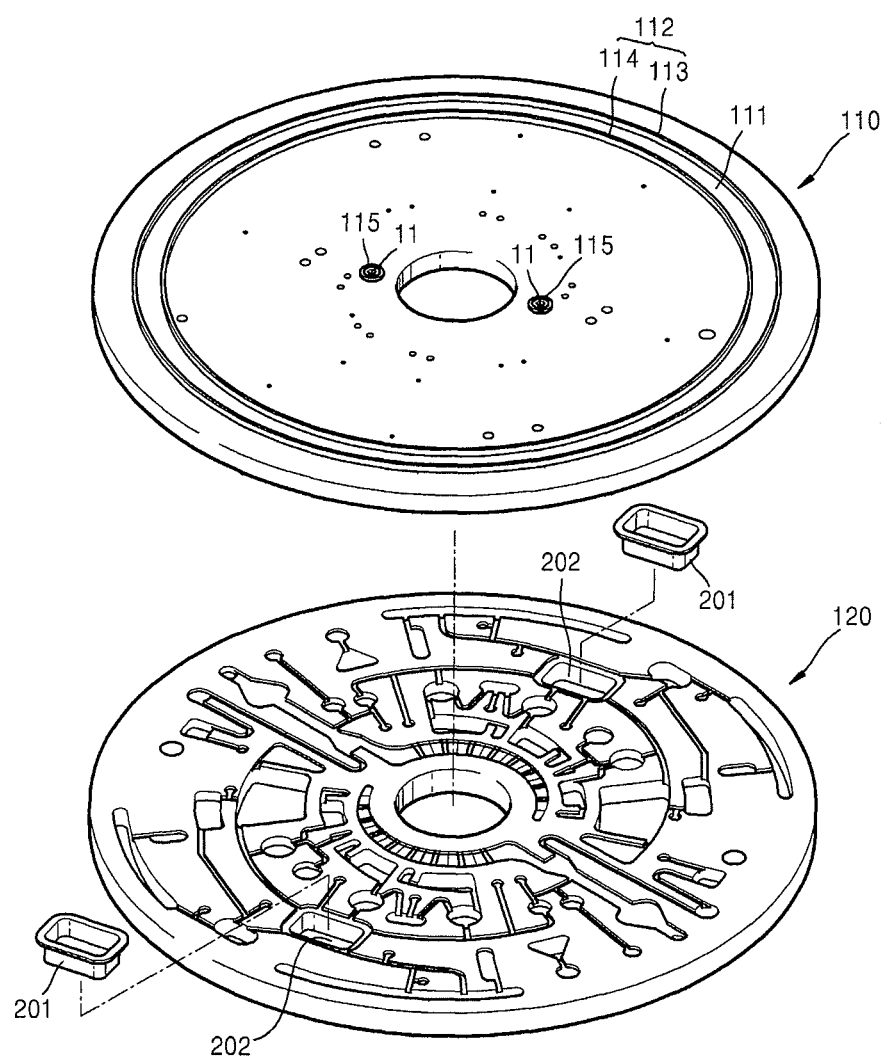
FIG. 6 is an exploded perspective view of the microfluidic apparatus of FIG. 1.

FIG. 6 is an exploded perspective view of the microfluidic apparatus of FIG. 1. Referring to FIG. 6, the platform 100 may include an upper plate 110 and a partition plate 120. The microfluidic structure including the chambers and channels shown in FIGS. 1 and 2A through 2D is formed on the partition plate 120. The chambers and channels formed on the partition plate 120 have closed lower portions and open upper portions. When reaction cartridges 201 are coupled to mounting portions 202 formed on the partition plate 120 as shown in FIGS. 3A and 3B, the reaction chamber 200 is formed. However, one or more embodiments are not limited to the above example, and the reaction chamber 200 may be formed by directly coating the surface of the mounting portion 202 with capture antibodies or antigens. In order to form the normally closed valve, the valve material V1 may be loaded into the corresponding channel C as shown in FIG. 4A. In order to form the normally open valve, the valve material V2 may be loaded into the valve chamber VC connecting to the corresponding channel C as shown in FIG. 5A.

A plurality of vent holes are formed in the upper plate 110 in order to make the fluid flow smoothly through the chambers and channels including the first through fourth vent chambers 215, 225, 235, and 245. In FIG. 6, the holes which are not denoted by reference numerals among the holes formed in the upper plate 110 denote the vent holes. Chambers facing the detector (520 of FIG. 10), for example, the first through fourth QC chambers 35, 50, 60, and 70 and the detection chambers 250, are located at the same distances in the radial direction from the center C. A protective unit 112 for protecting a region 111 which corresponds to the first through fourth QC chambers 35, 50, 60, and 70 and the detection chamber 250 may be formed on the upper plate 110. The protective unit 112 protects the region 111 from contamination, or reduces the chance of the region 111 being contaminated while the microfluidic apparatus is being handled. For example, the protective unit 112 may include a first rib 113 and a second rib 114 which protrude upward and surround the region 111. The upper plate 110 may further include a third rib 115 that protrudes upward in order to represent an inlet 11 that is connected to the sample chamber 10.

When the upper plate 110 is coupled to the partition plate 120, the microfluidic structure formed on the partition plate 120 has the closed upper and lower portions, and the valves controlling the flow of fluid are formed on corresponding locations. Therefore, the microfluidic structure, in which the fluid may be received and flow, is completed. The first, second, and third buffers and the washing buffer may be loaded into the first, second, and third buffer chambers 210, 220, and 230 and the washing buffer chamber 240 on the partition plate 120, respectively, and the upper plate 110 is coupled to the partition plate 120, and then, the microfluidic apparatus receiving the first, second, and third buffers and the washing buffer is fabricated. The upper plate 110 may be coupled to the partition plate 120 using adhesion, radio frequency welding, ultrasonic wave welding, laser welding, or ultraviolet ray bonding process. Alternatively, after coupling the upper plate 110 to the partition plate 120, the first, second, and third buffers and the washing buffer may be loaded into the first, second, and third buffer chambers 210, 220, and 230 and the washing buffer chamber 240 through inlets (not shown) formed in the upper plate 110 and the inlets may be blocked.

In order to form the normally closed valves and the normally open valves, the valve materials may be loaded into the channels C and the valve chambers VC, for example, through inlets (not shown) formed in the upper plate 110, after coupling the upper plate 110 to the partition plate 120.

Figure 7:
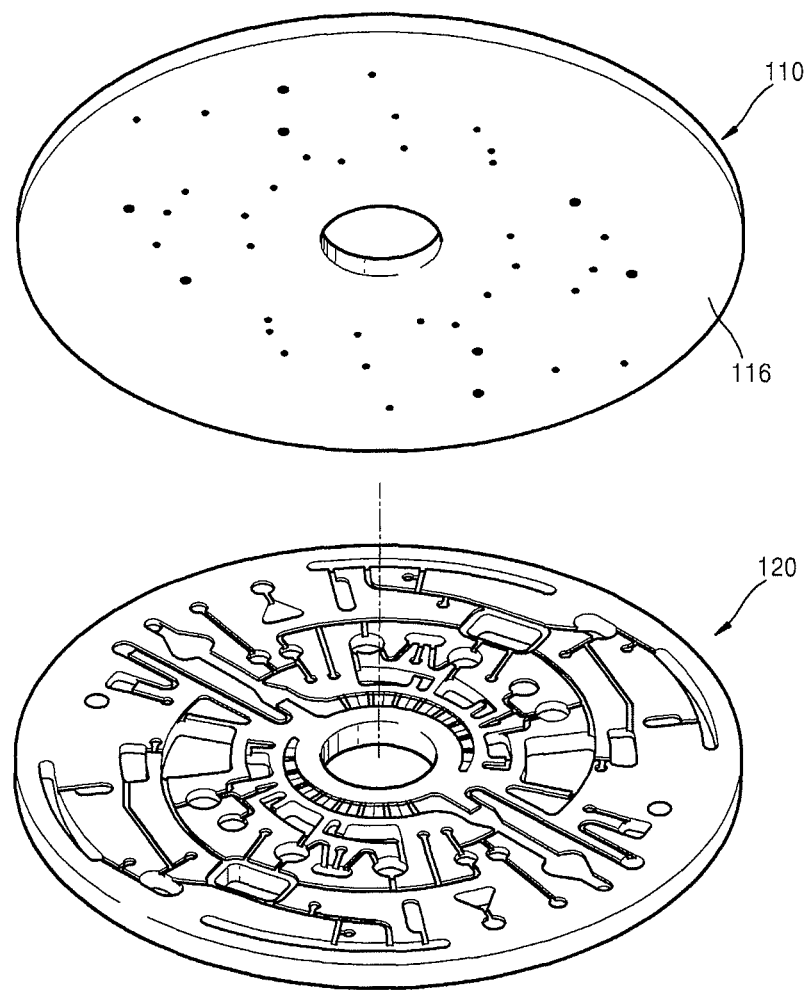
FIG. 7 is an exploded perspective view illustrating processes of forming the closed valve and the open valve in the microfluidic apparatus of FIG. 1.
Figure 8A:
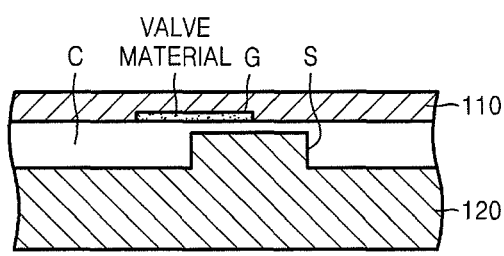
FIG. 8A is a cross-sectional view of the open valve fabricated by the processes illustrated in FIG. 7.
Figure 8B:
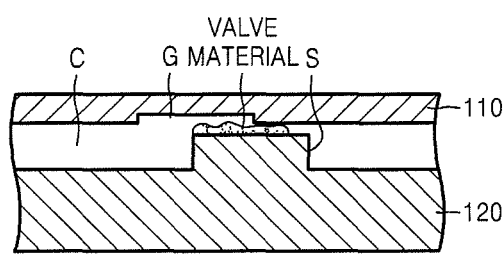
FIG. 8B is a cross-sectional view of the closed valve fabricated by the processes illustrated in FIG. 7.
Figure 8C:
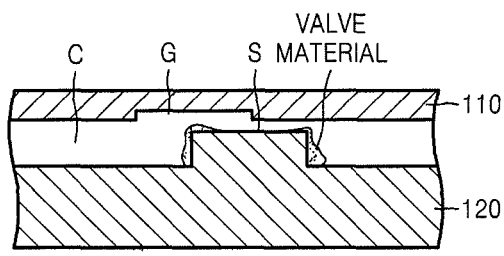
FIG. 8C is a cross-sectional view showing opening of the closed valve shown in FIG. 8B.

As another method of forming the normally closed valves and the normally open valves, the valve material is applied to a predetermined thickness on locations where the valves will be formed on a lower surface 116 of the upper plate 110 as shown in FIG. 7. After that, the upper plate 110 and the partition plate 120 are coupled to each other. In FIG. 7, tiny black circles denote the valve material for forming the normally closed valves, and black large circles denote the valve material for forming the normally open valves. FIG. 8A is a cross-sectional view of a portion where the valve is formed after coupling the upper plate 110 to the partition plate 120. Referring to FIG. 8A, since the valve material does not block the channel C, the normally open valve is formed when the upper plate 110 and the partition plate 120 are coupled to each other. In order to form the normally closed valve, the external energy is applied to the tiny black circles to melt the valve material. The external energy may be provided by the laser beam, for example. Then, as shown in FIG. 8B, the valve material is melted and coagulated while blocking the channel C, and thus, the normally closed valve is formed. In order to open the closed valve, the energy that is similar to the energy applied when the closed valve is formed, or a greater amount of energy, is applied to the valve material shown in FIG. 8B. Then, as shown in FIG. 8C, the valve material flows into the space in the channel C, and the channel C is opened. The processes of closing the channel C by operating the open valve shown in FIG. 8A will be clarified by considering the processes of forming the closed valve shown in FIG. 8B.

Figure 8D:
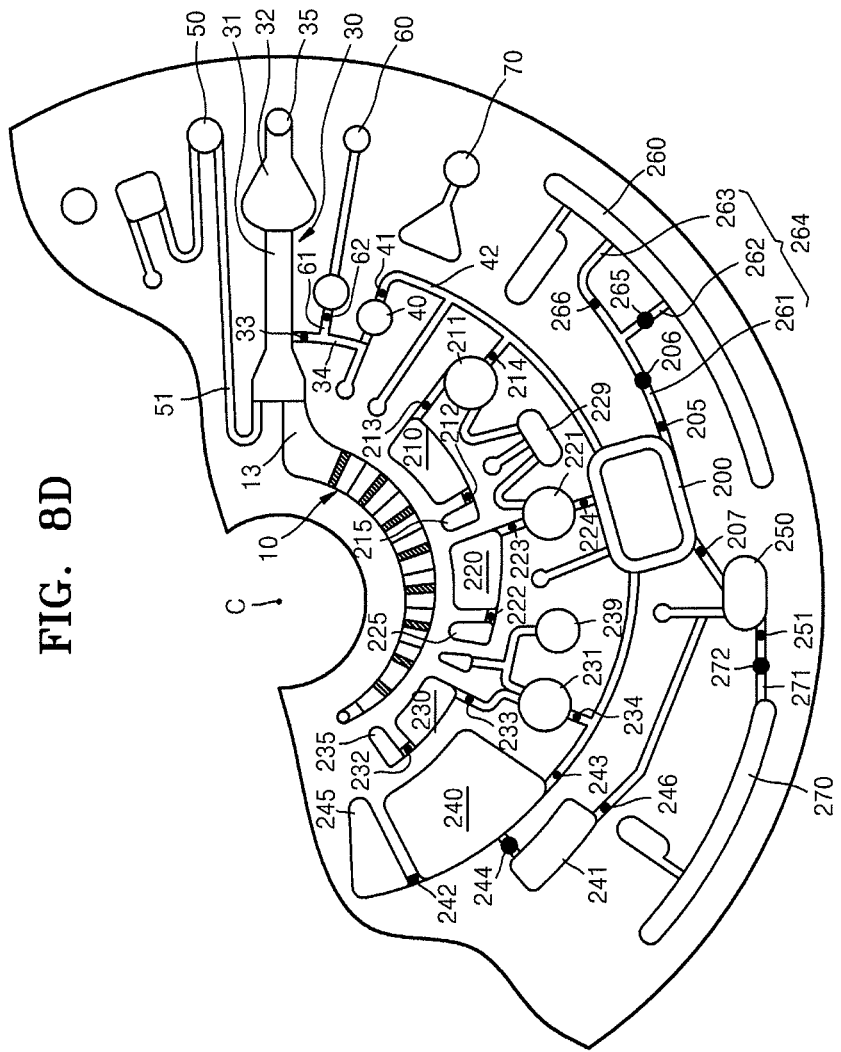
FIG. 8D is a view showing an example of a microfluidic apparatus adopting the valve fabricated by the processes illustrated in FIG. 7.

An example of the microfluidic apparatus including the normally closed valves and the normal open valves fabricated using the above described processes, is shown in FIG. 8D. Referring to FIG. 8D, the normally closed valves are represented as small black circles, and the normally open valves are represented as large black circles. The microfluidic apparatus of FIG. 8D is different from the microfluidic apparatus of FIG. 2A in that the normally open valves 206, 244, 265, and 272 are located in the channels that are to be closed. According to the above structure, there is no need to form the chambers (VC of FIG. 5A) for receiving the valve material (V2 of FIG. 5A) for forming the normally open valves, and thus, the structure of the microfluidic apparatus is simplified.

In the above embodiment, a groove G for applying the valve material to a predetermined thickness is formed in the upper plate 110, and a stepped portion S corresponding to the groove G is formed in the channel C of the partition plate 120, however, one or more embodiments are not limited to the above example. The groove G may not be formed on the bottom surface of the upper plate 110, and the stepped portion S may not be formed in the channel C of the partition plate 120. Even when the groove G and the stepped portion S are not formed, the normally open valve and the normally closed valve may be formed by adjusting the amount of valve material and the energy intensity for melting the valve material. The groove G may be a reference for locating the position where the valve material will be applied. The stepped portion S may facilitate flow of the melted valve material according to the capillary phenomenon when the closed valve is opened.

Figure 9:
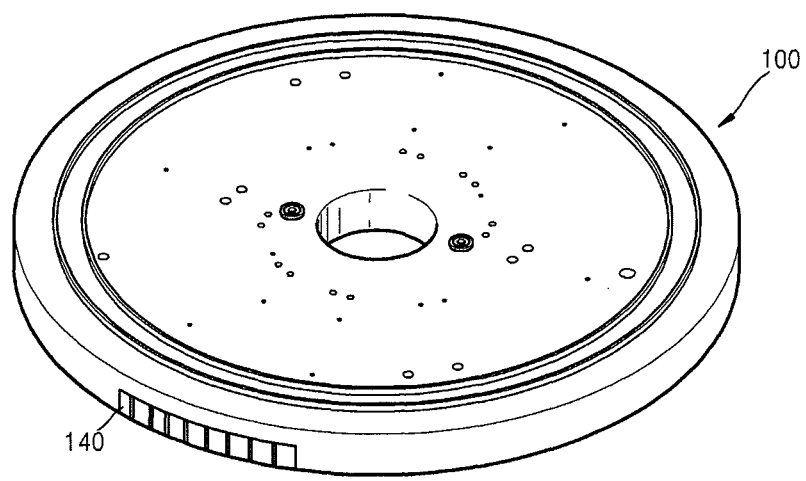
FIG. 9 is a perspective view of the microfluidic apparatus of FIG. 1.

FIG. 9 is a perspective view of the microfluidic apparatus fabricated by performing the above described processes. Referring to FIG. 9, a barcode 140 is disposed on a side portion of the platform 100. The barcode 140 may be attached to the side portion of the platform 100. The barcode 140 may include information about the fabrication data of the microfluidic apparatus, and a term of validity of the microfluidic apparatus. In addition, the barcode 140 may include data relating to a relation between the absorbance of the final resultant in the detection chamber 250 and a concentration.

FIG. 10 is a diagram of a sample testing system using the microfluidic apparatus. Referring to FIG. 10, the system may include a rotation driver 510, the detector 520, and an electromagnetic wave generator 530. The rotation driver 510 provides the microfluidic apparatus with a centrifugal force for centrifugating the sample and moving the fluid by rotating the microfluidic apparatus. The rotation driver 510 stops the microfluidic apparatus at a predetermined location so that the valves face the electromagnetic wave generator 530. The electromagnetic wave generator 530 operates the valves, and irradiates, for example, laser beams. The electromagnetic wave generator 530 may move in a radial direction of the microfluidic apparatus. In addition, the rotation driver 510 rotates the microfluidic apparatus so that the chambers face the detector 520 to detect the absorbance. The rotation driver 510 may include a motor drive device (not shown) that may control an angular position of the microfluidic apparatus. For example, the motor drive device may use a step motor or a direct current (DC) motor. The detector 520 senses optical characteristics such as a fluorescent property, a light emission property, and/or an absorbing property of the material that is to be detected. A barcode reader 540 reads the barcode 140 disposed on the side portion of the platform 100. The rotation driver 510, the detector 520, the electromagnetic wave generator 530, and the barcode reader 540 are located in a predetermined measuring chamber 550. A heater 560 is for maintaining a temperature in the measuring chamber 550 as the appropriate temperature for performing the testing. A controller 570 is provided for controlling the sample analyzing process.

Hereinafter, a sample testing method using the above microfluidic apparatus will be described. In the present embodiment, processes of detecting certain protein from blood, as an example, will be described.

<Sample Loading>

In the microfluidic apparatus of the present embodiment, buffers and a washing buffer used in the testing operation are loaded in advance. That is, the first buffer chamber 210 receives a conjugate buffer for performing the sandwich immunoassay. The second buffer chamber 220 may receive a substrate buffer which represents a predetermined color by performing a substrate reaction with the resultant of the conjugate reaction. The third buffer chamber 230 may receive a stop solution for stopping the substrate reaction. The washing buffer chamber 240 receives the washing buffer. Therefore, for performing the sample test, whole blood taken from a patient is loaded into the sample chamber 10 of the microfluidic apparatus, and the microfluidic apparatus is mounted on the rotation driver 510 to prepare for the sample test.

<Obtaining Barcode Information>

The information stored in the barcode 140 disposed on the side portion of the platform 100 is read using the barcode reader 540. It may be identified whether the microfluidic apparatus is valid from the information about the fabrication data of the microfluidic apparatus and the term of validity of the microfluidic apparatus stored in the barcode 140. When the microfluidic apparatus is not in condition for performing the valid test, the controller 570 may generate an alarm that informs a user that the microfluidic apparatus should be replaced. In addition, the information stored in the barcode 140 may include information about the relation between the measured absorbance and a concentration of the protein.

<Determining Whether Microfluidic Apparatus is Used>

An absorbance of the first QC chamber 35 disposed at an end portion of the sample separation unit 30 is measured using the detector 520. When the measured absorbance represents that the blood exists in the first QC chamber 35, it implies that the microfluidic apparatus was previously used. In this case, the controller 570 may generate the alarm that informs the user that the microfluidic apparatus should be replaced.

<Temperature Detection>

An absorbance of the fourth QC chamber 70 is measured using the detector 520. Since the thyon dye, the absorbance of which varies depending on the temperature, is accommodated into the fourth QC chamber 70, the temperature of the microfluidic apparatus may be checked using the absorbance of the fourth QC chamber 70. The microfluidic apparatus may be stored in cold storage at a temperature of about 4° C. in order to maintain activities of the first through third buffers in a state where the first through third buffers and the washing buffer are loaded into the microfluidic apparatus. Since the microfluidic apparatus that is kept cold cannot be used directly in the test, when the temperature of the microfluidic apparatus does not reach the appropriate temperature, for example, 20° C., the controller 570 drives the heater 560 to raise the temperature of the measuring chamber 550. After that, the processes of measuring the absorbance of the fourth QC chamber 70 and detecting the temperature of the microfluidic apparatus are repeated, and then, the test may be performed when the temperature reaches the appropriate temperature for performing the test. The number of repetitions may be set appropriately, and when the temperature does not reach the appropriate temperature even if the predetermined number of repetitions is performed, the controller 570 may generate an error message.

<Determining Whether an Amount of Sample is Appropriate>

The microfluidic apparatus is rotated at a low speed to convey the blood from the sample chamber 10 to the sample separation unit 30. The low speed is a rotation speed generating the centrifugal force that is suitable for conveying the fluid. After filling the sample separation unit 30, the blood is conveyed to the second QC chamber 50 through the channel 51. The detector 520 measures the absorbance of the second QC chamber 50. The absorbance varies depending on the amount of blood in the second QC chamber 50. When it is determined that the amount of blood is not sufficient from the absorbance of the second QC chamber 50, the controller 570 may generate an alarm which informs the user that more blood should be loaded into the sample chamber 10.

<Centrifugating Sample>

The rotation driver 510 rotates the microfluidic apparatus at a high speed. Here, the high rotation speed may divide the blood into blood serum or blood plasma, that is, the supernatant, and blood cells, that is, the precipitate. Then, the blood cells are moved to the precipitate collecting unit 32, and the supernatant remains in the supernatant collecting unit 31.

<Metering Supernatant>

The electromagnetic wave generator 530 irradiates the electromagnetic waves to the normally closed valve 33. Then, the valve material is melted and the valve 33 is opened as shown in FIG. 4B or 8C. The rotation driver 510 rotates the microfluidic apparatus to generate the centrifugal force. Then, the supernatant is moved to the supernatant metering chamber 40 from the supernatant collecting unit 31 through the channel 34. Since the valve 41 located at the outlet of the supernatant metering chamber 40 is normally closed, the supernatant fills the supernatant metering chamber 40. Therefore, when the amount of the supernatant is sufficient, the supernatant, the volume of which equals the volume of the supernatant metering chamber 40, is received in the supernatant metering chamber 40.

<Determining Quantity and Quality of Supernatant>

The valve 62 located in the inlet of the channel 61 is opened using the electromagnetic wave generator 530. When the microfluidic apparatus is rotated, the supernatant is induced into the third QC chamber 60 through the channel by the centrifugal force. The absorbance of the third QC chamber 60 is measured using the detector 520. When the measured absorbance is the reference absorbance, which indicates that a sufficient amount of supernatant is in the third QC chamber 60, it is determined that a sufficient amount of supernatant is received in the supernatant metering chamber 40. When the measured absorbance is greater than the reference absorbance, the supernatant may include impurities because the centrifugation of the sample is not performed properly or the sample is defective. In this case, the controller 570 may generate an alarm which informs the user that the microfluidic apparatus should be replaced and the test should be performed again. In addition, when the absorbance is less than the reference absorbance or greater than the reference absorbance, it may mean that the amount of supernatant received in the third QC chamber 60 is insufficient or the supernatant includes air pores. In this case, the amount received in the supernatant metering chamber 40 is insufficient. Therefore, the controller 570 may generate an alarm which informs the user that the microfluidic apparatus should be replaced and the test should be performed again.

<Determining Operation Error of the Valve 33>

When the absorbance of the third QC chamber 60 represents that the third QC chamber 60 is empty, it may mean that the valve 33 does not operate properly and the supernatant does not move to the supernatant metering chamber 40 and the third QC chamber 60. In this case, the valve 33 is driven using the electromagnetic wave generator 530 and the absorbance of the third QC chamber 60 may be measured again. When the same result is shown in the re-measuring process, the controller 570 indicates the operation error of the valve 33 and may generate an alarm which informs the user that the microfluidic apparatus should be replaced.

<Re-Detection of Temperature>

Before performing a process for detecting a specimen, the temperature of the microfluidic apparatus may be measured again. The antigen-antibody reaction for detecting the specimen may be performed well in a certain temperature range. For example, the antigen-antibody reaction for detecting the specimen from the bio-sample such as blood may be performed at a temperature of about 37° C. Therefore, the detector 520 may detect the absorbance of the fourth QC chamber 70 again to measure the temperature. When the temperature does not reach the temperature of about 37° C., the controller 570 drives the heater 560 to raise the temperature of the measuring chamber 550. After that, the process of detecting the absorbance of the fourth QC chamber 70 to measure the temperature of the microfluidic apparatus is repeated. When the temperature of the microfluidic apparatus reaches the temperature of about 37° C., the test may be continued. The number of times the temperature is re-measured may be set appropriately. If the temperature of the microfluidic apparatus is lower than 37° C. even when the temperature is measured again, the controller 570 may generate a temperature error message and terminate the test. Alternatively, the controller 570 may generate an alarm which informs the user that the microfluidic apparatus should be replaced.

<Performing Antigen-Antibody Reaction>

The valve 41 located at the outlet of the supernatant metering chamber 40 is opened using the electromagnetic wave generator 530. When the microfluidic apparatus is rotated, the supernatant received in the supernatant metering chamber 40 is moved to the reaction chamber 200 through the channel 42 due to the centrifugal force.

The valves 212 and 213 are opened using the electromagnetic wave generator 530. Then, the conjugate buffer is moved from the first buffer chamber 210 to the first metering chamber 211. Since the first buffer chamber 210 communicates with the external air via the valve 212 and the first vent chamber 215, the conjugate buffer may be easily moved to the first metering chamber 211. Since the valve 214 located at the outlet of the first metering chamber 211 is the normally closed valve, the conjugate buffer fills the first metering chamber 211 first. After that, excessive conjugate buffer is received in the first excessive buffer chamber 229. When the valve 214 located at the outlet of the first metering chamber 211 is opened using the electromagnetic wave generator 530, a fixed amount of conjugate buffer is moved to the reaction chamber 200.

In order to mix the supernatant with the conjugate buffer, the rotation driver 510 may perform a shaking operation of the microfluidic apparatus a few times. In the reaction chamber 200, a binding reaction among the specimen, the captured antibody, and secondary antibody included in the conjugate buffer is performed. After that, the valve 205 that is located on the outlet, which is located on a side of the first waste chamber 260, of the reaction chamber 200 is opened using the electromagnetic wave generator 530. The impurities except for the specimen captured by the capture antibody and the secondary antibody are moved to the first waste chamber 260 through the end portion 261 and the final end 262 of the first waste channel 264. After that, when the electromagnetic waves are irradiated onto the normally open valve 265 located at the final end 262 of the first waste channel 264, the valve material is melted and coagulated to close the valve 265 as shown in FIG. 5B or FIG. 8B. Since the normally open valve 265 located at the final end 262 of the first waste channel 264 is closed and the valve 266 located at the final end 263 is closed, and the reaction chamber 200 and the first waste chamber 260 are isolated from each other.

<Washing>

The valves 242 and 243 are opened using the electromagnetic wave generator 530. Then, the washing buffer is moved from the washing buffer chamber 240 to the reaction chamber 200. Since the washing buffer chamber 240 communicates with the external air via the valve 242 and the fourth vent chamber 245, the washing buffer may be easily moved to the reaction chamber 200. For performing the washing operation, the rotation driver 510 may perform a shaking operation of the microfluidic apparatus a few times. The valve 266 is opened using the electromagnetic wave generator 530. Then, the washing buffer in the reaction chamber 200 is moved to the first waste chamber 260 through the end portion 261 and the final end 263 of the first waste channel 264 with the reaction impurities. The normally open valve 206 located at the end portion 261 of the first waste channel 264 is closed using the electromagnetic wave generator 530. Accordingly, the reaction chamber 200 and the first waste chamber 260 are isolated from each other again.

<Obtaining Reference Absorbance>

Since the blank chamber 241 is connected to the washing buffer chamber 240 through the normally open valve 244, the washing buffer is also received in the blank chamber 241. The valve 246 located at the outlet of the blank chamber 241 is opened using the electromagnetic wave generator 530. When the microfluidic apparatus is rotated, the washing chamber received in the blank chamber 241 is moved to the detection chamber 250. Since the blank chamber 241 is in communication with the external air via the open valve 244, the washing buffer chamber 240, the valve 242 that is opened in advance, and the fourth vent chamber 245, the washing buffer may be easily moved to the detection chamber 250. The detector 520 measures the absorbance of the detection chamber 250. The measured absorbance becomes the reference absorbance representing the state of the detection chamber 250. The valve 251 located at the outlet of the detection chamber 250 is opened using the electromagnetic wave generator 530. Then, the washing buffer is moved from the detection chamber 250 to the second waste chamber 270 through the second waste channel 271. After that, the open valve 272 located at the inlet of the second waste chamber 270 is closed using the electromagnetic wave generator 530. Accordingly, the detection chamber 250 and the second waste chamber 270 are isolated from each other. In addition, the open valve 244 located at the inlet of the blank chamber 241 is closed using the electromagnetic wave generator 530. Therefore, the detection chamber 250 and the blank chamber 241 are isolated from each other.

<Determining the Wrong Operation of the Valve 246>

If the absorbance represents the empty state of the detection chamber 250 during the process of obtaining the reference absorbance, it may mean that the valve 246 does not operate properly. In this case, the process of obtaining the reference absorbance may be repeated. When the same error is repeatedly generated, the controller 570 may generate an alarm which informs the user that the microfluidic apparatus should be replaced. The number of repetitions may be set appropriately.

<Substrate Reaction>

The valves 222 and 223 are opened using the electromagnetic wave generator 530. Then, the substrate buffer is moved from the second buffer chamber 220 to the second metering chamber 221. Since the second buffer chamber 220 is in communication with the external air via the valve 222 and the second vent chamber 225, the substrate buffer may be easily moved to the second metering chamber 221. Since the valve 224 located at the outlet of the second metering chamber 221 is closed, the substrate buffer fills the second metering chamber 221 first. The excessive substrate buffer is received in the first excess buffer chamber 229. When the closed valve 224 located at the outlet of the second metering chamber 221 is opened using the electromagnetic wave generator 530, the weighed amount of the substrate buffer is moved to the reaction chamber 200. The rotation driver 510 may perform a shaking operation of the microfluidic apparatus a few times in order to mix the substrate buffer with the resultant of the antigen-antibody reaction in the reaction chamber 200. Due to the substrate reaction, the mixture in the reaction chamber 200 has the color corresponding to the amount of the specimen.

<Reaction Stop>

The valves 232 and 233 are opened using the electromagnetic wave generator 530. Then, the stop buffer is moved from the third buffer chamber 230 to the third metering chamber 231. Since the third buffer chamber 230 is in communication with the external air via the valve 232 and the third vent chamber 235, the stop buffer may be easily moved to the third metering chamber 231. Since the valve 234 located at the outlet of the third metering chamber 231 is the closed valve, the stop buffer fills the third metering chamber 231 first. After that, the excessive stop buffer is received in the second excess buffer chamber 239. When the valve 244 located at the outlet of the third metering chamber 231 is opened using the electromagnetic wave generator 530, the metered amount of stop buffer is moved to the reaction chamber 200. In order to mix the stop buffer with the resultant of the antigen-antibody reaction in the reaction chamber 200 and the substrate buffer, the rotation driver 510 may perform a shaking operation of the microfluidic apparatus a few times. The substrate reaction is suspended by the stop buffer.

<Detecting Concentration of Specimen>

The closed valve 207 located at the outlet, which is located at a side of the detection chamber 250, of the reaction chamber 200 is opened using the electromagnetic wave generator 530. Then, the final fluid is moved to the detection chamber 250. The absorbance of the detection chamber 250 is measured using the detector 520. At this time, the absorbance is measured a few times at predetermined time intervals in order to obtain the final absorbance which does not change. The controller 570 calculates the concentration of the specimen by using the difference between the obtained absorbance and the reference absorbance, from the information relating to the concentration of protein according to the absorbance stored in the barcode 140.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A microfluidic apparatus comprising:
   a sample chamber;
   a sample separation unit which receives a sample from the sample chamber and separates a supernatant from the sample by using a centrifugal force, said sample separation unit including a linear shaped supernatant collecting portion and a precipitate collecting portion, wherein the precipitate collecting portion is wider than the linear shaped supernatant collecting portion;
   a testing unit comprising a detection chamber, in which a resultant of an antigen-antibody reaction between the supernatant, capture antibody or capture antigen, and a reaction buffer is received; and
   a first quality control chamber for identifying reliability in specimen detection,
   wherein the first quality control chamber is directly connected to the sample separation unit,
   wherein the first quality control chamber, directly connected to the sample separation unit, has a single point of entry from the sample separation unit and the first quality control chamber is wholly disposed more distally from the sample chamber than the supernatant collecting portion and the precipitate collecting portion of the sample separation unit.

2. The microfluidic apparatus of claim 1, wherein the first quality control chamber is disposed at a final end of the sample separation unit for identifying whether the microfluidic apparatus has been previously used by detecting absorbance.

3. The microfluidic apparatus of claim 2, further comprising a second quality control chamber which is connected to the sample separation unit and receives a portion of the sample exceeding a capacity of the sample separation unit.

4. The microfluidic apparatus of claim 3, further comprising a third quality control chamber which is connected to a channel that connects the reaction chamber to the sample separation unit to detect a state of the supernatant.

5. The microfluidic apparatus of claim 1, further comprising a fourth QC chamber which receives a material having an absorbance of which varies depending on temperature.

6. The microfluidic apparatus of claim 1, further comprising a rotatable platform on which the sample chamber, the sample separation unit, the testing unit and the first quality control chamber are formed,
wherein the detection chamber and the first quality control chamber are located at a same distance from a center of rotation in a radial direction of the platform.

7. The microfluidic apparatus of claim 6, wherein the platform comprises:
a partition plate, on which an engraved structure providing spaces for receiving a fluid and for forming channels through which the fluid flows and having an opened upper portion is formed, and
an upper plate coupled to the upper portion of the partition plate to block the upper portion of the engraved structure.

8. The microfluidic apparatus of claim 7, wherein the upper plate comprises a protective unit which protects regions corresponding to the detection chamber and the first quality control chamber from being contaminated.

9. The microfluidic apparatus of claim 8, wherein the protective unit comprises ribs surrounding the regions corresponding to the detection chamber and the first quality control chamber.

* * * * *